United States Patent [19]

Tabor et al.

[11] Patent Number: 5,498,523
[45] Date of Patent: Mar. 12, 1996

[54] DNA SEQUENCING WITH PYROPHOSPHATASE

[75] Inventors: Stanley Tabor, Cambridge; Charles C. Richardson, Chestnut Hill, both of Mass.

[73] Assignee: President and Fellows of Harvard College, Cambridge, Mass.

[21] Appl. No.: 275,339

[22] Filed: Jul. 14, 1994

Related U.S. Application Data

[63] Continuation of Ser. No. 37,475, Mar. 24, 1993, abandoned, which is a continuation of Ser. No. 922,355, Jul. 29, 1992, abandoned, which is a continuation of Ser. No. 808,055, Dec. 12, 1991, abandoned, which is a continuation of Ser. No. 336,751, Apr. 12, 1989, abandoned, which is a continuation-in-part of Ser. No. 218,103, Jul. 12, 1988, Pat. No. 4,962,020.

[51] Int. Cl.$^6$ .............. C12Q 1/68; C12P 19/34; G01N 33/50; C12N 9/14
[52] U.S. Cl. .............. 435/6; 435/91.5; 435/194; 435/195; 435/21; 436/94; 935/77; 935/78
[58] Field of Search .............. 435/6, 91.5, 91.2, 435/194, 195, 15, 18, 21; 436/94; 935/16, 17, 77, 78

[56] References Cited

U.S. PATENT DOCUMENTS

| | | | |
|---|---|---|---|
| 4,572,894 | 2/1986 | Imahori et al. | 435/68 |
| 4,683,195 | 7/1987 | Mullis et al. | 435/6 |
| 4,683,202 | 7/1987 | Mullis | 435/91 |
| 4,795,699 | 1/1989 | Tabor | 435/5 |
| 4,800,159 | 1/1989 | Mullis et al. | 435/172.3 |
| 5,001,050 | 3/1990 | Blanco | 435/5 |

FOREIGN PATENT DOCUMENTS 0258017  8/1987  European Pat. Off. .

OTHER PUBLICATIONS

Freifelder, D. Ie; Molecular Biology, (1987) Jones & Bartlett Publishers, Inc., Boston, Mass. pp. 234–235.

Saiki et al. "Primer–Directed Enzymatic Amplification of DNA with a Thermostable DNA Polymerase", Science, vol. 239, pp. 487–490, 1988.

*Primary Examiner*—W. Gary Jones
*Assistant Examiner*—Carla Myers
*Attorney, Agent, or Firm*—Lyon & Lyon

[57] ABSTRACT

A kit or solution for use in extension of an oligonucleotide primer having a first single-stranded region on a template molecule having a second single-stranded region homologous to the first single-stranded region, comprising a first agent able to cause extension of the first single-stranded region of the primer on the second single-stranded region of the template in a reaction mixture, and a second agent able to reduce the amount of pyrophosphate in the reaction mixture below the amount produced during the extension in the absence of the second agent.

7 Claims, No Drawings

DNA SEQUENCING WITH PYROPHOSPHATASE

BACKGROUND OF THE INVENTION

This invention was made with government support including a grant from Department of Energy Grant No. DE-SG02-88ER60688 and U.S. Public Health Service Grant No. A1-06045. The U.S. government has certain rights to the invention.

This application is a continuation of Ser. No. 08/037,475, filed Mar. 24, 1993, now abandoned, which is a continuation of Ser. No. 07/922,355, filed Jul. 29, 1992, now abandoned, which is a continuation of Ser. No. 07/808,055, filed Dec. 12, 1991, now abandoned, which is a continuation of Ser. No. 07/336,751, filed Apr. 12, 1989, now abandoned, which is a continuation-in-part of Ser. No. 07/218,103, filed Jul. 12, 1988, issued as U.S. Pat. No. 4,962,020, which is hereby incorporated by reference to herein.

This invention relates to methods for performing a primer extension reaction, such as a DNA sequencing reaction, or a polymerase chain reaction.

In a primer extension reaction an oligonucleotide primer having homology to a single-stranded template DNA, e.g., genomic DNA, is caused to anneal to the template DNA. The annealed mixture is then provided with a DNA polymerase in the presence of nucleoside triphosphates under conditions in which the DNA polymerase extends the primer to form a complementary DNA strand to the template DNA. In a DNA sequencing reaction, the primer is extended in the presence of a chain-terminating agent, e.g., a dideoxynucleoside triphosphate, to cause base-specific termination of the primer extension. Sanger et al., 74 Proc. Nat'l. Acad. Sci. 5463, 1977. In a polymerase chain reaction two primers are provided, each having homology to opposite strands of a double-stranded DNA molecule. After the primers are extended, they are separated from their templates, and additional primers caused to anneal to the templates and the extended primers. The additional primers are then extended. The steps of separating, annealing, and extending are repeated in order to amplify the number of copies of template DNA. Saiki et al., 239 Science 487, 1988.

SUMMARY OF THE INVENTION

In a first aspect, the invention features a solution or kit for use in extension of an oligonucleotide primer having a first single-stranded region on a template molecule having a second single-stranded region, the first and second regions being homologous. The solution or kit includes a first agent able to cause extension of the first single stranded region of the primer on the second single-stranded region of the template in a reaction mixture, and a second agent able to reduce the level of pyrophosphate in the reaction mixture below the level produced during extension in the absence of the second agent.

By solution is meant any aqueous and/or buffered liquid containing the components described above. These components are present in the solution at concentrations sufficient to perform their desired function. For example, the first agent is present at a concentration sufficient to reduce the level of pyrophosphate in the solution. By kit is meant a container which holds one or more of the components of the solution separately. For example, the first and second agents are held in separate containers in solutions adapted to be mixed together.

By causing extension of the oligonucleotide primer is meant performing a reaction in which an oligonucleotide primer having a single-stranded region is annealed, or naturally occurs in the annealed state, with another nucleic acid molecule which acts as a template upon which the oligonucleotide primer can be extended by addition of nucleoside triphosphates to form nucleic acid homologous to the template nucleic acid. Generally, extension entails providing a DNA polymerase or RNA polymerase to covalently add nucleotides to the primer.

A reaction mixture is any solution or solid phase suitable for performing an extension reaction. Generally, it is a liquid buffer containing nucleoside or deoxynucleoside triphosphates and metal ions required for an extension reaction. The mixture may also contain any standard buffering agents and, for a DNA sequencing reaction, one or more dideoxynucleoside triphosphates, or an equivalent chain-terminating agent.

By reducing the level of pyrophosphate is meant that the amount of pyrophosphate in the reaction mixture is reduced to an amount which has little or no significant effect on the extension of the primer on the template. That is, the level of pyrophosphate is low enough to reduce pyrophosphorolysis to an insignificant level (less than 10% the level of pyrophosphorolysis in the presence of 300 µM pyrophosphate). Preferably, the level of pyrophosphate is reduced to below 25 µM, even more preferably to below 5 µM. This phase is meant to include use of an agent, such as a pyrophosphatase, which acts to prevent the build-up of pyrophosphate, as well as remove it from a solution.

By homologous is meant that the two single-stranded regions are able to form sufficient non-covalent bonds between their respective nucleotides to form a stable double-stranded structure under conditions normally used for annealing nucleic acids, and for performing a primer extension reaction.

In preferred embodiments, the first agent is a DNA polymerase, most preferably chosen from Klenow, Taq polymerase, a T7-type DNA polymerase (i.e., a polymerase similar to that in a phage in which the DNA polymerase requires host thioredoxin as a subunit, e.g., T7 DNA polymerase or the DNA polymerase of T3, ΦI, ΦII, H, W31, gh-1, Y, AA1122, or Sp6), T4 DNA polymerase, T5 DNA polymerase, Φ29 DNA polymerase and reverse transcriptase; the second agent is an enzyme, most preferably a pyrophosphatase, for example, a pyrophosphatase resistant to heating at between 60° C. and 95° C.

In a second aspect, the invention features an improved method for extending an oligonucleotide primer having a first single-stranded region on a template molecule having a second single-stranded region, including providing a first agent able to cause extension of the primer on the template. The improvement is provision of a second agent able to reduce the amount of pyrophosphate below the amount produced during extension in the absence of the second agent.

In preferred embodiments, the method includes the steps of providing at least one or two oligonucleotide primers having single-stranded regions and at least one or two template molecules having single-stranded regions, and annealing the single-stranded regions of the primers and the templates to form an annealed mixture. The resulting annealed mixture is provided with the first and second agents to cause extension of the primers. The annealed mixture may also be provided with a dideoxynucleoside triphosphate. The method may further include the step of separating the primers from the templates after their extension, and repeating the steps of providing primers, extending the primers, and separating the primers.

In a related aspect, the invention features a method for amplifying DNA, including performing a polymerase chain reaction in the presence of an agent able to reduce the amount of pyrophosphate in the reaction below the amount produced during a polymerase chain reaction in the absence of the agent. Preferably, the agent is a pyrophosphatase.

In another related aspect, the invention features a method for amplifying DNA including providing a solution of Φ29 DNA polymerase, a DNA to be amplified, and an agent able to reduce the amount of pyrophosphate in the solution below that amount produced in the absence of the agent.

Applicants have determined that pyrophosphorolysis, where an oligonucleotide chain is reduced in length, is detrimental to a primer extension reaction. The pyrophosphorolysis is caused by the availability of pyrophosphate. For example, a polymerase chain reaction, as described by Cetus (European Patent Application 0,258,017) and by Saiki et al., 239 Science 487, 1988, is inhibited by addition of pyrophosphate even at very low concentrations. This pyrophosphorolysis can be prevented by providing an agent, for example, a pyrophosphatase, capable of removing pyrophosphate. Addition of pyrophosphatase to a polymerase chain reaction greatly enhances the progress of that reaction, and provides superior results compared to use of the method without a pyrophosphatase. Similarly addition of a pyrophophatase to a DNA sequencing reaction provides more uniformity in intensities of bands formed in a polyacrylamide gel used to identify products of the sequencing reaction. This uniformity is due to prevention of degradation of specific DNA products by pyrophosphorolysis.

Other features and advantages of the invention will be apparent from the following description of the preferred embodiment thereof, and from the claims.

DESCRIPTION OF THE PREFERRED EMBODIMENTS

Any agent which is capable of inhibiting a pyrophosphorolysis reaction is useful in this invention. One way to inhibit pyrophosphorolysis is to break down any pyrophosphate that is generated during a polymerase reaction, by adding the enzyme pyrophosphatase. Even trace addition of a pyrophosphatase (one thousanth the molar ratio of DNA polymerase molecules in a solution) to a primer extension reaction completely stabilizes oligonucleotide fragments produced in a polymerase reaction, by preventing pyrophosphorolysis. The agent should be added at a concentration sufficient to either catalyze the hydrolysis of pyrophosphate in the reaction mixture at a rate that will prevent accumulation of pyrophosphate to a level that will lead to pyrophosphorolysis, or prevent accumulation of pyrophosphate in any other manner. The amount of agent needed is readily determined by standard techniques.

There follows an example of the use of pyrophosphatase in a polymerase chain reaction. This example is not limiting to this invention; those skilled in the art will recognize that any primer extension reaction will be benefited by the addition of an agent as described above. Similarly, the use of pyrophosphatase in the examples below is not limiting to this invention, other agents suitable for reducing the effect of excess pyrophosphate in a primer extension reaction are readily identified by those skilled in the art. The relative concentrations of primer, DNA polymerase, and pyrophosphatase suitable in the invention are readily determined by routine experimentation, and are well known to those in the art.

It is preferable that a pyrophosphatase used in this invention be resistant to heating at high temperatures, since high temperatures are used in a polymerase chain reaction, for example, temperatures between 95° C. to 100° C., although temperatures between 65° C. and 95° C. are also commonly used. Thus, it is advantageous to provide a pyrophosphate resistant to heating at 65° C. to 95° C. Such a pyrophosphatase can be readily obtained from any bacterium that is naturally able to grow and flourish at high temperatures, e.g., *Thermus aquaticus*. Most bacteria have naturally-occurring pyrophosphatases, and those existing in natural environments at high temperatures will therefore be suitable sources of this enzyme.

Use of a pyrophosphatase in a polymerase chain reaction as described below with Taq polymerase allows the reaction to run to completion—that is, to cause depletion of all the provided deoxynucleoside triphosphates. This allows diagnostic techniques which make use of a polymerase chain reaction to be automated. Assay for progress of the reaction can entail measurement of the generation of phosphate or the generation of DNA from the deoxynucleoside triphosphates (for example, by acid precipitation), both of which are simple and quick assays, instead of the necessity to run a gel to detect the product of the polymerase chain reaction.

EXAMPLE 1

PCR Reaction with Pyrophophatase

In this example DNA termed M13 Trx-F (the actual DNA used is not critical in this invention) was amplified by provision of a forward and reverse primer using a polymerase chain reaction as follows. This method is generally described in Saiki et. el., supra. Trx-F DNA at a concentration of 0.4 picomoles was mixed with 1 μl Tris (1M, pH 8.5), 10 μl magnesium chloride (15 mM), 6.7 μl of four deoxynucleoside triphosphates (3 mM), 10 μl of forward primer (10 picomole; from ALN), 20μ, reverse primer (10 picomole, New England BioLabs), 2 μl gelatin (0.5%), and 55 μl distilled water. 0.5 μl of Taq polymerase (12 units, U.S. Biochemicals, Cleveland, Ohio) was then added and the solution heated to 94° C. for one minute, 50° C. for one minute, and 72° C., for two minutes and this cycle of heating repeated 40 times. Identical reactions were run in the absence or presence of pyrophosphate at various concentrations (12 μM, 37 μM, 333 μM, and 1 mM) and in the presence of pyrophosphatase (yeast inorganic pyrophosphatase from Sigma, Catalog No. 1-4503, used without purification, or used after purification on an FPLC mono Q column). Another source of pyrophosphatase is Worthington yeast inorganic pyrophosphatase without further purification. Generally, 0.001 units of yeast inorganic pyrophosphate (4 ng) are suitable in a reaction as described above. This amount may of course be considerably greater, and may be less. The range of concentrations is readily determined by routine experimentation. The concentration need only be enough to lower the level of pyrophosphate below about 5–50 μM.

In the above reaction, pyrophosphate inhibited the polymerase chain reaction at levels of 25 μM or greater. Pyrophosphatase reversed this inhibition and stimulated production of the polymerase chain reaction products by approximately two fold.

EXAMPLE 2

Preparation of Heat Resistant Pyrophosphatase

This is an example of purification of an inorganic pyrophosphatase from cells of *Thermus aquaticus*. Cells of *T. aquaticus* were obtained from the American Type Culture Collection. 10 liters of cells were grown at 70° C. using the growth medium of Chien et al. 127 J. Bacteriol. 1550 (1976). The cells were harvested (~20 gm), resuspended in 40 ml of 10% sucrose, 50 mM Tris HCl, pH 7.5, 5 mM EDTA; lysed by three passages through a French press, and cell debris removed by centrifugation at 30,000 rpm, for 60 min in a Beckman 50 Ti rotor. The supernatant was treated with streptomycin sulfate to remove DNA. 4 ml of a 40% streptomycin solution was added to 40 ml supernatant, mixed for 30 min., and centrifuged for 30 min at 8,000 rpm. The resulting supernatant was then treated with ammonium sulfate. No pyrophosphatase activity was precipitated at 60% ammonium sulfate, but all was precipitated by 70% ammonium sulfate: To 19 ml of supernatant 7.2 gm ammonium sulfate (60%) was added, mixed for 30 min., and spun for 30 min. at 8,000 rpm. To the supernatant 3 gm ammonium sulfate (70%) was added, mixed for 30 min., and spun for 30 min. at 8,000 rpm. The pellet was resuspended in 20 ml 20 mM Tris-HCl pH 7.5, 1 mM EDTA, 10% glycerol, 10 mM 2-mercaptoethanol (Buffer A) and then dialyzed overnight against 2 liters of Buffer A. The dialysate was passed over a DEAE DE52 column (100 ml) equilibrated in Buffer A, washed with 300 ml of Buffer A+50 mM NaCl, and then run in a liter gradient of buffer A containing from 50 mM to 500 mM NaCl. The pyrophophatase eluted at buffer A containing 125 mM NaCl. The eluate (60 mL) was dialyzed against 2 liters of 20 mM $KPO_4$ pH 7.4, 1 mM EDTA, 10 mM 2-mercaptoethanol, 10% glycerol (Buffer B) and loaded onto a phosphocellulose column (100 ml) equilibrated in buffer B. All of the pyrophosphatase activity flowed through the column. This flow-through was then dialyzed against 20 mM Tris HCl pH 7.0, 1 mM EDTA, 10% glycerol (Buffer C), and applied to an FPLC monoQ column in buffer C. A gradient, in Buffer C, containing 100 mM NaCl to 250 mM NaCl was run and the pyrophosphatase activity eluted at 180 mM NaCl. Fractions with pyrophosphatase activity were dialyzed against 20 mM $KPO_4$ pH 7,4, 0.1 mM EDTA, 50% glycerol, and stored at –20° C.

This pyrophosphatase activity was not affected by 40 cycles of a polymerase chain reaction, with each cycle containing a 95° C., 1 min. heating step. Further, the pyrophosphatase did not hydrolyze dNTPs, nor was it inhibited by dNTPs in the reaction mixture. The pyrophosphatase activity was assayed generally as described by Chen et al. 28 Anal. Chem. 1756 (1956), and Josse, 241J. Biol. Chem. 1938 (1966).

OTHER EMBODIMENTS

Other embodiments are within the following claims. For example, enzymes which use a protein primer rather than a DNA primer, e.g., Φ29 DNA polymerase which polymerizes double stranded DNA, can be used to amplify DNA without need for denaturing heating steps or reannealing steps. Blanco et al., DNA replication and mutagenesis, A.S.M. Chapter 12, 1988. Inclusion of a pyrophosphatase, or its equivalent, in such an amplification reaction will enhance the yield of DNA amplified in this system.

We claim:

1. A solution for use in a DNA sequencing reaction, comprising a DNA polymerase, a chain terminating agent, and a pyrophosphatase.

2. The solution of claim 1, wherein said pyrophosphatase retains activity at a temperature between 60° C. and 95° C.

3. An improved method for performing DNA sequencing reactions, including providing a DNA polymerase, the improvement comprising:

performing the DNA sequencing reaction in the presence of an added pyrophosphatase and DNA polymerase.

4. The method of claim 3, wherein said method further comprises the step of providing a dideoxynucleoside triphosphate.

5. The solution of claim 1 wherein said DNA polymerase is chosen from T7 DNA polymerase, reverse transcriptase, and Φ29 DNA polymerase.

6. The method of claim 3 wherein said DNA polymerase is chosen from T7 DNA polymerase, reverse transcriptase, and Φ29 DNA polymerase.

7. The solution of claim 1, wherein said chain terminating agent is a dideoxynucleoside triphosphate.

* * * * *